United States Patent
Wynn

(10) Patent No.: US 6,977,365 B1
(45) Date of Patent: Dec. 20, 2005

(54) PHOTOMETRIC DETECTOR ASSEMBLY WITH AUTOMATED CALIBRATION FILTERS

(75) Inventor: William H. Wynn, Hillsborough, CA (US)

(73) Assignee: Wedgewood Analytical Inc., Anaheim, CA (US)

( * ) Notice: Subject to any disclaimer, the term of this patent is extended or adjusted under 35 U.S.C. 154(b) by 31 days.

(21) Appl. No.: 10/354,156

(22) Filed: Jan. 28, 2003

(51) Int. Cl.[7] ............ H01J 3/14; H01J 40/14; H01J 5/16
(52) U.S. Cl. ............ 250/216; 250/239; 356/416
(58) Field of Search .............. 250/216, 239, 250/226, 573–576; 356/416, 418, 419, 438, 356/440, 228

(56) References Cited

U.S. PATENT DOCUMENTS

| | | | |
|---|---|---|---|
| 4,078,896 A | * | 3/1978 | Moen et al. ............ 422/91 |
| 4,583,859 A | | 4/1986 | Hall, II |
| 5,760,911 A | | 6/1998 | Santschi et al. |
| 5,905,271 A | | 5/1999 | Wynn |
| 6,153,873 A | * | 11/2000 | Wolf ............ 250/208.1 |
| 6,512,223 B1 | | 1/2003 | Wynn |

* cited by examiner

*Primary Examiner*—David Porta
*Assistant Examiner*—Seung C. Sohn
(74) *Attorney, Agent, or Firm*—Dorsey & Whitney LLP

(57) ABSTRACT

Photometric detector assembly which includes a housing, means for passing an optical beam along a path through the housing to a detector, a NIST traceable calibration filter enclosed within the housing, and a remotely operable actuator for moving the filter into and out of the beam path.

19 Claims, 4 Drawing Sheets

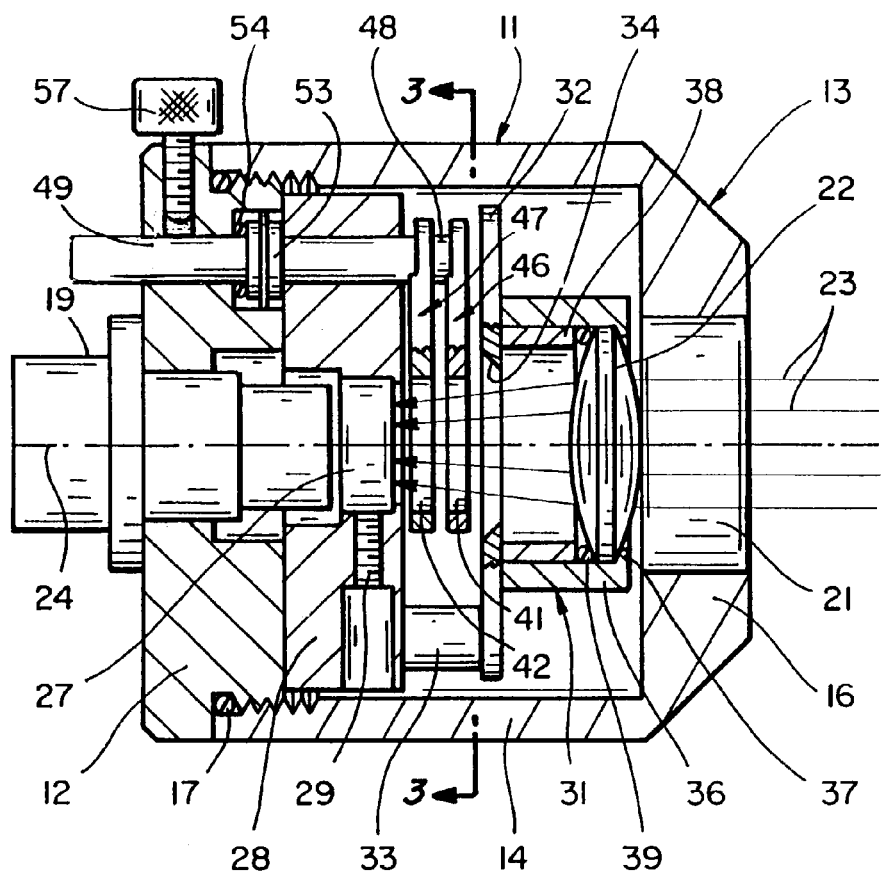
FIG_1
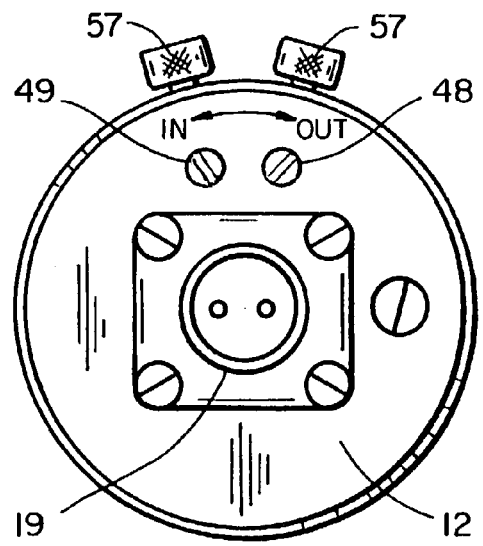
FIG_2

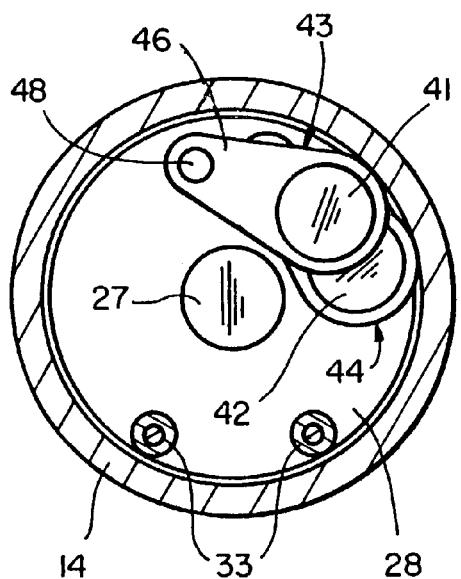
FIG_3A
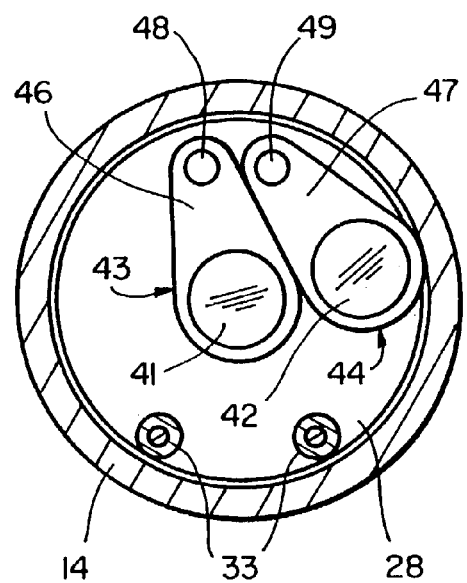
FIG_3B
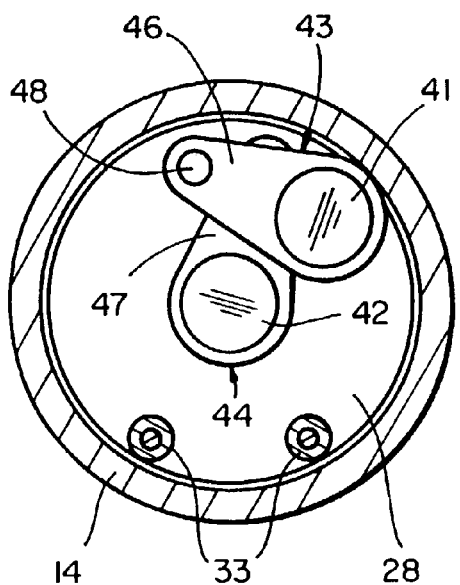
FIG_3C
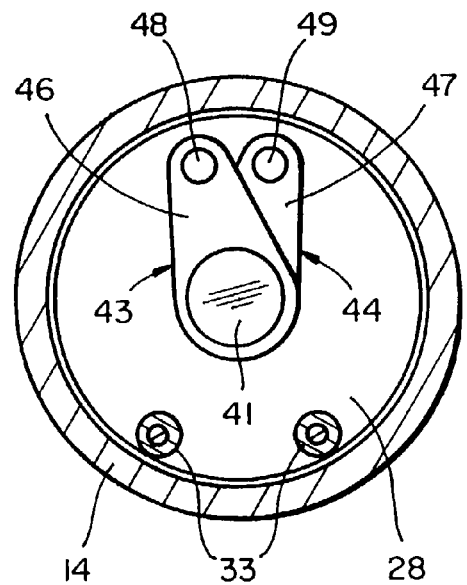
FIG_3D

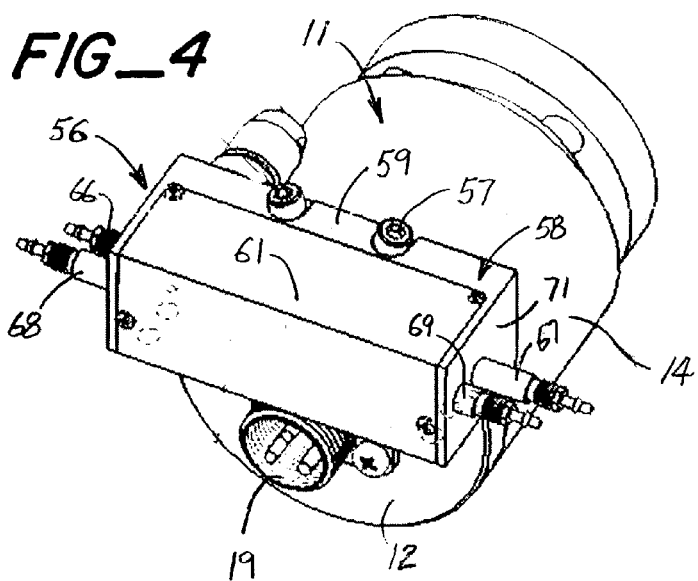
FIG_4
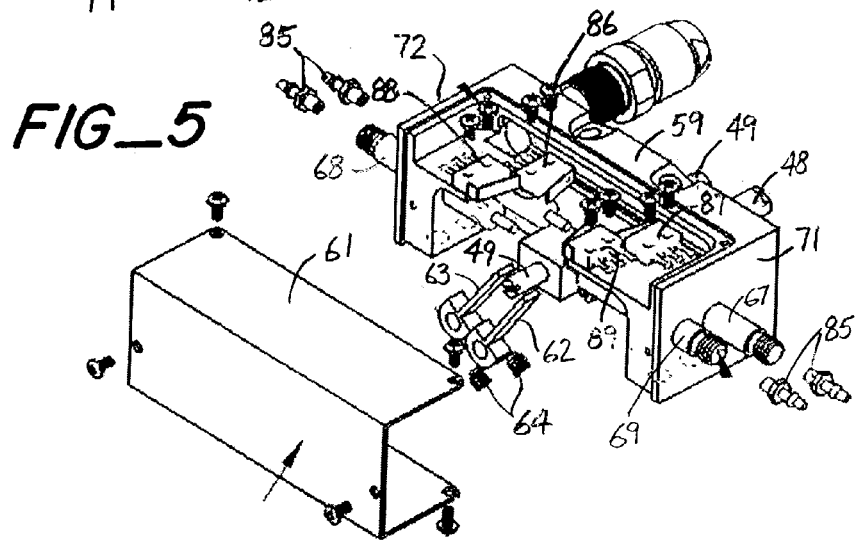
FIG_5
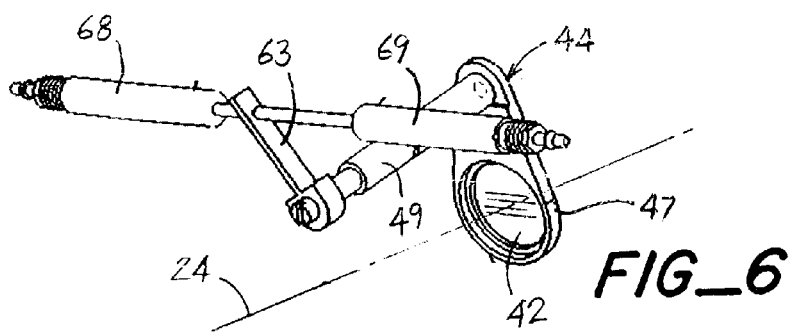
FIG_6

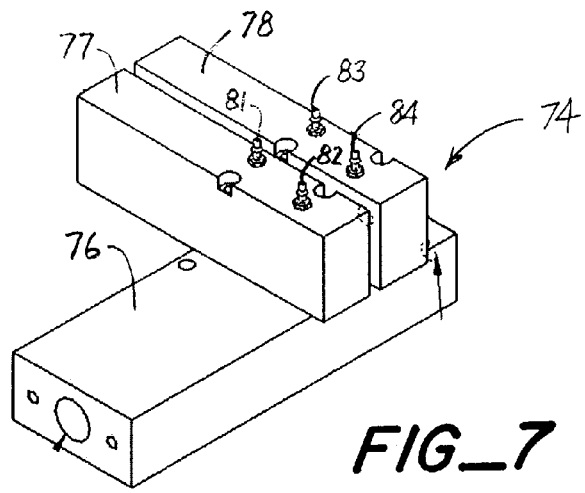
FIG_7
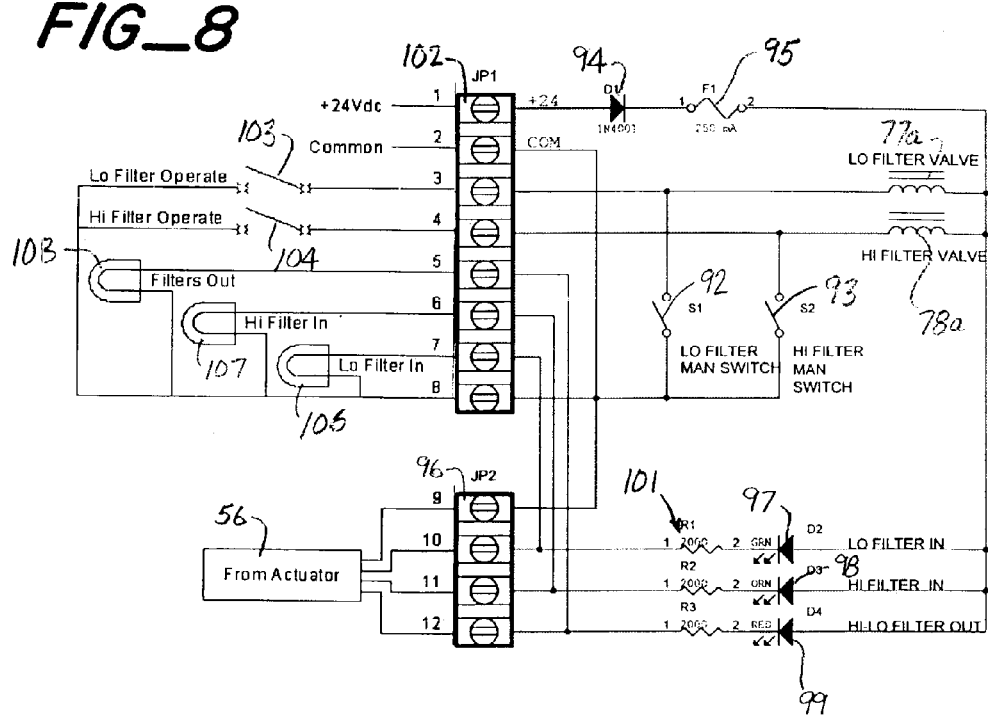
FIG_8

PHOTOMETRIC DETECTOR ASSEMBLY WITH AUTOMATED CALIBRATION FILTERS

BACKGROUND OF THE INVENTION

1. Field of Invention

This invention pertains generally to photometric analyzers and, more particularly, to a photometric detector assembly with automated calibration filters for use in a photometric analyzer such as an inline optical sensor.

2. Related Art

U.S. Pat. No. 5,905,271 discloses an inline optical sensor which can be utilized in a wide variety of applications (e.g. spectrophotometers, colorimeters, turbidimeters, refractometers, and ultrasonic flow and particle sensing devices) for monitoring photometric the properties of a fluid product stream. Such instruments generally have a light source and a detector positioned on opposite sides of the product stream, with the light source directing a beam of light through the product stream to the detector. The light can be in the ultra violet, visible or near infrared spectrums, and the term light is used herein as including all three.

When inline photometric analyzers are used as a primary measurement source for controlling critical filtration and separation processes, particularly in the biotech and pharmaceutical fields, NIST traceable calibration standards must generally be used in order to comply with validation protocols and procedures. Such standards are typically in the form of filters which are placed between the light source and detector. These filters are subject to deterioration with use and exposure to the environment, and they must be re-certified periodically.

U.S. Pat. No. 6,512,223 discloses a photometric detector assembly which includes a pair of NIST traceable calibration filters enclosed within a sealed housing and means outside the housing for manually moving the filters into and out of the path of a beam between calibration and normal operating positions. This system can be calibrated to a high degree of accuracy, and being in sealed housing and exposed to the beam only on a limited basis, the filters do not need to be cleaned and/or replaced as often as they otherwise would. However, it movement the filters between the calibration and operating positions is a manual operation.

OBJECTS AND SUMMARY OF THE INVENTION

It is in general an object of the invention to provide a new and improved detector assembly for use in a photometric analyzer.

Another object of the invention is to provide a photometric detector assembly of the above character which has automated calibration filters.

There and other objects are achieved in accordance with the invention by providing a photometric detector having a housing, means for passing an optical beam along a path through the housing to a detector, a filter enclosed within the housing, and a remotely operable actuator for moving the filter into and out of the beam path.

BRIEF DESCRIPTION OF THE DRAWINGS

FIG. 1 is a cross-sectional view of one embodiment of a photometric detector assembly incorporating the invention, with the actuator removed for ease of illustration.

FIG. 2 is an end elevational view of the embodiment of FIG. 1.

FIGS. 3A–3D are operational cross-sectional views taken along line 3—3 in FIG. 1.

FIG. 4 is an isometric view of the embodiment of FIG. 1, with the actuator in place.

FIG. 5 is an exploded isometric view of the actuator in the embodiment of FIGS. 1 and 4.

FIG. 6 is an isometric view of the mechanism for moving one of the calibration filters into and out of a beam path in the embodiment of FIGS. 1 and 4.

FIG. 7 is an isometric view, somewhat schematic, of a 4-way control valve and manifold assembly for the pneumatic operating cylinders which adjust the position of the calibration filters in the embodiment of FIGS. 1 and 4.

FIG. 8 is a wiring diagram of a circuit for controlling operation of the valves in the embodiment of FIG. 7.

The photometric detector assembly shown in FIGS. 1–3 is similar to an embodiment shown in the corresponding figures of U.S. Pat. No. 6,512,223. As illustrated in those figures, the actuator includes a housing 11 which consists of a circular base plate 12 and a cover 13 which is threadedly mounted on the base plate. The cover includes a cylindrical side wall 14 and an end wall 16. An O-ring 17 provides a seal between the base plate and the cover.

A measurement detector 19 is mounted on the base plate, and an optically transparent window 21 is mounted in the end wall in axial alignment with the measurement detector. An objective lens 22 directs a beam 23 passing through the window along an optical axis or path 24 within the housing and focuses it on the detector. An optical filter 27 is positioned in front of the detector in a mounting block 28 which is bolted onto the base plate. The filter is retained in the mounting block by a set screw 29.

The mount 31 for objective lens 22 includes a mounting plate 32 which is affixed to mounting block 28 and separated from it by spacers 33. The mounting plate has an aperture 34 for the beam passing between the lens and the detector. The mount also includes a cylindrical barrel 36 which extends in a forward direction from the mounting plate, with a radial flange 37 at the outer end of the barrel. The lens is clamped between that flange and a cylindrical spacer 38 within the barrel, with an O-ring 39 between the outer end of the spacer and the lens.

A pair of NIST traceable calibration filters 41, 42 are mounted within the housing for movement into and out of optical path 24. These filters are standards whose calibration is part of an unbroken chain of comparison with standards maintained by the National Institute of Standards and Technology. They can be either neutral density filters or color filters, depending upon the application for which the detector is to be used. They are calibrated and certified to the measurement wavelength.

The calibration filters are mounted on positioners 43, 44 comprising teardrop-shaped holders 46, 47 affixed to shafts 48, 49. The shafts are rotatively mounted in base plate 12 and mounting block 28 and extend through the base plate so they are accessible externally of the housing. Friction assemblies 53 and O-rings 54 are mounted on the shafts for holding the filters in the positions to which they are set.

The filters are movable between the normal operating position shown in FIG. 3A in which both filters are positioned out of the path of the beam and the calibration positions shown in FIGS. 3B–3D in which one or both of the filters are positioned in the beam path. When the filters are in the normal operating position, they are positioned out of the field of view of the measurement detector, and they are protected from optical radiation by lens mounting plate 32. In the calibration position, they are aligned with the aperture 34 in the lens mounting plate and with the detector.

The detector assembly is particularly suitable for use with an inline optical sensor of the type shown in U.S. Pat. No. 5,905,271, the disclosure of which is incorporated herein by reference. That sensor is particularly advantageous because it provides highly accurate vernier adjustments of the positions of the light source and detector windows on opposite sides of the chamber in which the product stream is monitored.

For purposes of illustrating the calibration procedure, it is assembled that filter 41 has an optical density of 0.5 OD and that filter 42 has an optical density of 1.0 OD. With a non-absorbing liquid in the sample chamber and both filters in their OUT positions, i.e. the normal operation position shown in FIG. 3A, an absorbance monitor connected to the detector is adjusted to give a reading of 0.00. With filter 41 rotated to its IN position and filter 42 in its OUT position, as illustrated in FIG. 3B, the monitor reading should be 0.5 OD. When filter 41 is rotated to its OUT position and filter 42 is rotated to its IN position, as shown in FIG. 3C, the monitor reading should be 1.0 OD. Finally, when both filters are rotated to their IN positions, as shown in FIG. 3D, the monitor will read the sum of the two filter densities, or 1.5 OD. This three point calibration procedure checks both accuracy and linearity of the optical system. The calibration can be done with the sensor inline, so it is not necessary to remove the sensor to calibrate it.

As illustrated in FIG. 4, an actuator assembly 56 is mounted on detector housing 11 and secured in place by screws 57. In the embodiment illustrated, the actuator assembly has a generally rectangular housing 58 consisting of a base 59 and a cover 61.

Actuator arms 62, 63 are mounted on the outer end portions of filter positioning shafts 48, 49, and affixed thereto by setscrews 64. The actuator arms are driven by small, pneumatically operated cylinders 66–69 which are mounted on the end walls 71, 72 of housing 58. The operating cylinders are arranged in axially aligned pairs 66, 67 and 68, 69, with the output shafts of cylinders 66, 67 engaging opposite sides of actuator arm 62, and the shafts of cylinders 68, 69 engaging actuator arm 63.

Operation of the air cylinders is controlled by a solenoid-operated 4-way pneumatic valve assembly 74. As illustrated in FIG. 7, this assembly comprises a manifold 76 to which a pair of control valves 77, 78 are connected. The manifold is connected to a source of dry air (not show) at a regulated pressure on the order of 20–30 psig. Each of the valves has two output ports which are connected to the operating cylinders for one of the filter positioners. Thus, valve 77 has output ports 81, 82 which are connected to cylinders 66, 67 for moving filter 41 between its IN and OUT positions relative to beam path 24. Similarly, valve 78 has output ports 83, 84 which are connected to cylinders 68, 69 for moving filter 42 between its IN and OUT positions. Connections between the valves and the cylinders are made by conventional air hoses and fittings 85.

The positions of the actuator arms and, hence, the filters are monitored by micro switches 86–89 which are actuated when the arms reach the ends of their travel. The positional relationship between the arms and the filters is known, and the arms swing through an angle on the order of 45–60 degrees between the micro switches. Thus, the micro switches serve as limit switches as well as indicating the positions of the filters.

Operation of the valves is controlled by a control 91 which is illustrated in FIG. 8. This circuit includes manually operable switches 92, 93 which are connected electrically in series with the operating coils 77a, 78a of valves 77, 78. Operating current is supplied to the control circuit from a low voltage DC source, through a diode 94 and a fuse 95.

The micro switches in actuator 56 are connected to the control circuit via a terminal strip 96, and the positions of the filters are indicated by light emitting diodes (LEDs) 97–99 in the control circuit. Thus, LED 97 is illuminated when filter 41 is in the path of the beam, LED 98 is illuminated when filter 42 is in the path of the beam, and LED 99 is illuminated when neither of the filters is in the beam path. It desired, the three LEDs can be different colors, e.g. green, orange and red, as indicated in the drawing. Current through the LEDs is limited by resistors 101.

Operation of the valves can also be controlled remotely, and FIG. 8 shows an external control connected to the control circuit through a terminal strip 102 for that purpose. The remote control includes switches 103, 104 which are connected in parallel with switches 92, 93 and panel lights 106–108 which are connected in parallel with LEDs 97–99. Thus, valve 77 can be operated to move filter 41 either by local switch 92 or by remote switch 103, and valve 78 can be operated to move filter 42 either by local switch 93 or by remote switch 104. The positions of the filters are indicated both by LEDs 97–99 and by panel lights 106–108.

The invention has a number of important features and advantages. It provides a remotely operable actuator for in situ calibration of process instruments using filters and/or other optical devices such as attenuators. It translates linear motion to angular motion, and the dual inline cylinders which drive the actuator arms provide positive filter positioning and, hence, greater accuracy than a single operator. The micro switches which determine the end of travel further ensure proper positioning of the filters.

Being pneumatically operated, the actuator can be used in hazardous, e.g. explosive, environments due to its intrinsically safe design. It can also be used in either single beam or dual beam applications, and it can be utilized with either linear or angular solenoids.

Moreover, since the calibration filters are enclosed within a sealed housing and are exposed to the optical beam only on a limited basis, they do not have to be re-certified as often as they otherwise would.

Although the invention has been disclosed with specific reference to calibration filters in an optical measurement system, it can also be used in other applications and/or for positioning other optical devices such as attenuators.

It is apparent from the foregoing that a new and improved photometric detector assembly has been provided. While only certain presently preferred embodiments have been described in detail, as will be apparent to those familiar with the art, certain changes and modifications can be made without departing from the scope of the invention as defined by the following claims.

What is claimed is:

1. A photometric detector assembly, comprising a housing, a detector within the housing, means for passing an optical beam along a path through the housing to the detector, first and second calibration elements having respective optical attenuation spectra enclosed within the housing, and a remotely operable actuator coupled to the first and second calibration elements for moving the first and second calibration elements singularly or in combination into and out of the beam path.

2. The photometric detector assembly of claim 1 wherein the first calibration element is a NIST traceable calibration standard.

3. The photometric detector assembly of claim 1 wherein the first calibration element is mounted on a shaft which extends through a wall of the housing, and the actuator includes a radially extending arm affixed to the shaft externally of the housing, and a pair of oppositely aligned linear operators which engage opposite sides of the arm for rotating the shaft through a predetermined angle to move the first calibration element into and out of the beam path.

4. The photometric detector assembly of claim 3 wherein the linear operators are pneumatic cylinders.

5. The photometric detector assembly of claim 3 including limit switches which are actuated by the arm to stop the rotation of the shaft when the shaft reaches predetermined positions.

6. The photometric detector assembly of claim 1 wherein the actuator includes a control circuit.

7. In a photometric detector assembly: a housing having a circular base plate and a cylindrical cover with an end wall facing the base plate, a detector mounted on the base plate, a window in the end wall in axial alignment with the detector, an optical path extending through the housing between the window and the detector, a calibration filter mounted on a shaft which extends through the base plate, and a remotely operable actuator connected to the shaft outside the housing for moving the filter into and out of the beam path.

8. The photometric detector assembly of claim 7 wherein the actuator includes a radially extending arm affixed to the shaft, and a pair of oppositely aligned linear operators which engage opposite sides of the arm for rotating the shaft through a predetermined angle to move the filter into and out of the beam path.

9. The photometric detector assembly of claim 8 wherein the linear operators are pneumatic cylinders.

10. The photometric detector assembly of claim 8 including limit switches which are actuated by the arm to stop the rotation of the shaft when the shaft reaches predetermined positions.

11. The photometric detector assembly of claim 7 wherein a second filter is mounted on a second shaft which extends through the base plate, and the actuator is also connected to the second shaft for moving the second filter into and out of the beam path.

12. The photometric detector assembly of claim 7 wherein the filter is a NIST traceable calibration standard.

13. In a photometric detector assembly: a housing, a detector mounted in the housing, a window in the housing, an objective lens mounted within the housing near the window for directing an optical beam along a path to the detector, first and second calibration filters mounted on shafts which extend through a wall of the housing, and an actuator having linear operators coupled to the shafts outside the housing for rotating the shafts to move the filters into and out of the beam path.

14. The photometric detector of claim 13 wherein the linear operators are arranged in oppositely aligned pairs, and the actuator is coupled to the shafts by radially extending arms which are affixed to the shafts and engaged on opposite sides by the operators in the respective pairs.

15. The photometric detector of claim 14 including limit switches which are actuated by the arms to stop the rotation of the shafts when the shaft reach predetermined positions.

16. A photometric detector assembly, comprising a housing, means for passing an optical beam along a path through the housing to a detector, a filter enclosed within the housing, and a remotely operable actuator for moving the filter into and out of the beam path, the filter being mounted in a shaft which extends through a wall of the housing and the actuator including a radially extending arm affixed to the shaft externally of the housing, and a pair of oppositely aligned linear operators which engage opposite sides of the arm for rotating the shaft through a predetermined angle to move the filter into and out of the beam path.

17. The photometric detector assembly of claim 16 wherein the linear operators are pneumatic cylinders.

18. The photometric detector assembly of claim 16 including limit switches which are actuated by the arm to stop the rotation of the shaft when the shaft reaches predetermined positions.

19. The photometric detector assembly of claim 16 wherein the remotely operable actuator includes a control circuit.

* * * * *